United States Patent
Kizoulis et al.

(10) Patent No.: US 8,080,265 B2
(45) Date of Patent: Dec. 20, 2011

(54) COMPOSITIONS AND METHODS FOR TREATING SIGNS OF SKIN AGING

(75) Inventors: Menas G. Kizoulis, Bound Brook, NJ (US); Michael Southall, Lawrenceville, NJ (US); Samantha D. Tucker-Samaras, Long Valley, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 210 days.

(21) Appl. No.: 12/390,102

(22) Filed: Feb. 20, 2009

(65) Prior Publication Data

US 2010/0215785 A1    Aug. 26, 2010

(51) Int. Cl.
*A61K 36/45* (2006.01)
*A61K 36/00* (2006.01)

(52) U.S. Cl. ............ 424/732; 424/776; 424/425

(58) Field of Classification Search ............ None
See application file for complete search history.

(56) References Cited

U.S. PATENT DOCUMENTS

| | | | |
|---|---|---|---|
| 6,365,630 B1 | 4/2002 | Fisher et al. | |
| 2007/0196523 A1 | 8/2007 | Koganov | |
| 2008/0095719 A1* | 4/2008 | Herrmann et al. | 424/48 |
| 2010/0239695 A1* | 9/2010 | Vielhaber et al. | 424/765 |

FOREIGN PATENT DOCUMENTS

| | | |
|---|---|---|
| GB | 2 402 676 A | 12/2004 |
| GB | 2 438 999 A | 12/2007 |
| RU | 2180232 | 3/2002 |
| RU | 2297237 | 4/2007 |
| WO | WO 2005/123101 A1 | 12/2005 |

OTHER PUBLICATIONS

Cenizo, Valerie, et al., "LOXL as a Target to Increase the Elastin Content in Adult Skin: A Dill Extract Induces the LOXL Gene Expression", *Experimental Dermatology*, 2006, 15(8):574-81.
Chung, Jin Ho, et al., "Modulation of Skin Collagen Metabolism in Aged and Photoaged Human Skin in Vivo", *J. Invest. Dermatol.*, 2001, 117:1218-1224.
Ejeil, Anne-Laure, et al., "Expression of Matrix Metalloproteinases (MMPs) and Tissue Inhibitors of Metalloproteinases (TIMPs) in Healthy and Diseased Human Gingiva", *Journal of Periodontology*, 2003, 74(2):188-195.
Hermann, M., et al., "Blackberry Leaf Extract: A New Anti-Aging Active", *SOFW-Journal*, 2006, 132:42-46.
Kubota, T., et al., "Expression of mRNA for Matrix Metalloproteinases and Tissue Inhibitors of Metalloproteinases in Periodontitis-Affected Human Gingivial Tissue", *Archives of Oral Biology*, Mar. 1996, 41(3):253-262.
Lamaison, J.L., et al., "Tannin Content and Elastase Inhibiting Activity in the Rosaceae Family", *Ann. Pharmaceutiques Francaises*, 1990, 48(6):335-340.
Liu, Rugao., et al., "Retinoic Acid Increases Elastin in Neonanatal Rat Lung Fibroblast Cultures", *American Journal of Physiology*, Nov. 1993, 265(5):430-7.
Liu, Xiaoqing, et al., "Elastic Fiber Homeostasis Requires lysyl Oxidase-like 1 Protein", *Nature Genetics*, Feb. 2004, 36(2):178-182.
Thibodeau, Alain, "Metalloproteinase Inhibitors", *Cosmetics & Toiletries*, Nov. 2000, 115(11):75-82.

* cited by examiner

*Primary Examiner* — Christopher R. Tate
*Assistant Examiner* — Deborah A. Davis

(57) ABSTRACT

The invention relates to methods and compositions for treating skin aging, said compositions comprising at least one tropoelastin promoter and at least one tropoelastin crosslinker.

4 Claims, No Drawings

COMPOSITIONS AND METHODS FOR TREATING SIGNS OF SKIN AGING

FIELD OF THE INVENTION

The invention relates to methods and compositions for treating skin aging. More specifically, the invention relates to methods and compositions for (i) stimulating the production of tropoelastin and (ii) crosslinking tropoelastin at the same time.

BACKGROUND OF THE INVENTION

The aging of skin may be understood as being influenced by intrinsic factors and extrinsic factors. Intrinsic factors include natural changes to the skin, which are regulated by genetic makeup. Extrinsic factors include exogenous influences such as UV damage, environmental factors, and the like.

Aging of the skin can adversely affect elasticity and strength of the skin through changes in the two main constituents of the dermal extracellular matrix, the fibrous proteins collagen and elastin. For example, elastin is a large fibrous protein formed by the crosslinking of elastin precursor protein molecules (e.g., tropoelastin) into spiral filaments. The spiral filaments consist of peptidic chains that are capable of extending and then resuming their original shape.

Elastin is secreted by the fibroblasts of the dermal connective tissues into the extracellular matrix. However, the biosynthesis of elastin typically ceases at some point during adulthood. Furthermore, during intrinsic and extrinsic aging processes, elastin undergoes structural and compositional changes, e.g., the elastic fibers progressively degenerate and separate into fragments. The changes could manifest themselves by signs of aging, such as lines, wrinkles, loss of elasticity, sagging, skin dryness and unevenness, blotches, and age spots.

Certain agents are known for their beneficial effect of inhibiting the degradation of crosslinked elastin. For example, it is known that matrix metalloproteinases (MMPs), a group of enzymes that are able to break down macromolecules in the extracellular matrix, play an important role in elastin degradation. It has been found that the content of MMPs is markedly higher in old skin than in young skin. MMPs also play a critical role in the premature skin aging caused by exogenous factors. An even higher level of MMPs was detected in light-aged skin as compared with aged skin protected from the light. J. H. Chung et al., *J. Invest. Dermatol.* (2001) 117, 1218-1224. Studies have also shown that the levels of a series of matrix metalloproteinases (MMP-1, -3, -9 and -13) are significantly higher in patients with inflammation. T. Kuboto et al., *Arch. Oral. Biol.* (1996) 41, 253-262; A. L. Ejeil et al., *J. Periodontol.* (2003) 74, 188-195. Further, MMP-2 and MMP-9 were found to be the elastin-degrading proteases. *Cosmetics & Toiletries* (2000) 115 (11), 75-82).

A number of plant extracts have been described as inhibitors of various MMPs. For instance, J. L. Lamaison describes the inhibition of elastase (porcine pancreatic elastase) with extracts of plants selected from the rosaceae group and attributes the inhibition to the tannins they contain. *Ann. Pharmaceutiques Francaises* (1990) 48, 335-340.

M. Herrmann et al. discloses that SymMatrix, a hydroalcoholic blackberry leaf extract, exhibits the MMP-1, MMP-2, and MMP-9 inhibitory activity. *SOFW Journal* (2006) 132 (4), 42-46.

In addition, certain natural or synthetic compounds are known for the beneficial effect of promoting the production of elastin precursor. For example, retinoids up-regulate elastin production in fibroblasts. Liu B, Harvey C S, McGowan S E. *Am. J. Physiol.* (1993 November) 265(5 Pt 1):L430-437.

Furthermore, it has also been noted that certain agents positively influence the cross-linking of tropoelastin. For example, lysyl oxidase serves as a crosslinking enzyme and an element of the scaffold to ensure spatially defined deposition of elastin. Liu, Xiaoqing et al., Nature Genetics (2004), 36(2), 178-182. Cenizo et al. discloses a dill extract that induces the lysyl oxidase (LOXL) gene expression, which is responsible for elastin cross-linking in adults. Experimental Dermatology (2006), 15(8), 574-81. Additionally, currant, cardamon, black radish, box holly, *Asea foetida* gum, ethyl hexenoate, methyl butyrate, and ethyl decadienoate are disclosed as promoters of LOXL gene expression. GB 2,438,999.

Thus, numerous pathways and agents have been proposed to positively influence elastin and skin-properties related thereto. However, the inventors have recognized that a surprisingly beneficial synergistic efficacy is obtained by topically applying a composition that includes both a tropoelastin promoter and a tropoelastin crosslinker.

SUMMARY OF THE INVENTION

The present invention relates to compositions and methods to treat signs of skin aging. According to one aspect of the invention, a composition comprises at least one tropoelastin promoter and at least one tropoelastin crosslinker.

According to another embodiment of the invention, a method of treating a sign of skin aging comprises topically applying to skin in need thereof a cosmetically effective amount of composition comprising at least one tropoelastin promoter and at least one tropoelastin crosslinker.

Other features and advantages of the present invention will be apparent from the detailed description of the invention and from the claims.

DETAILED DESCRIPTION OF PREFERRED EMBODIMENTS

Unless defined otherwise, all technical and scientific terms used herein have the same meaning as commonly understood by one of ordinary skill in the art to which the invention belongs. Also, all publications, patent applications, patents, and other references mentioned herein are incorporated by reference. Unless otherwise indicated, a percentage refers to a percentage by weight (i.e., % (W/W)). As used herein, "signs of skin aging" includes the presence of lines and wrinkles, loss of elasticity, uneven skin, blotchiness, and age spots.

As used herein, "treating" refers to mitigating, reducing, preventing, improving, or eliminating the presence or appearance of a condition or disease.

As used herein, "wrinkle" includes fine lines, fine wrinkles, or coarse wrinkles. Examples of wrinkles include, but are not limited to, fine lines around the eyes (e.g., "crow's feet"), forehead and cheek wrinkles, frown-lines, and laugh-lines around the mouth.

As used herein, "loss of elasticity" includes loss of elasticity or structural integrity of the skin or tissue, including but not limited to sagging, lax and loose tissue. The loss of elasticity or tissue structure integrity may be a result of a number of factors, including but not limited to disease, aging, hormonal changes, mechanical trauma, environmental damage, or the result of an application of products, such as a cosmetics or pharmaceuticals, to the tissue.

As used herein, "uneven skin" means a condition of the skin associated with diffuse or mottled pigmentation, which may be classified as hyperpigmentation, such as post-inflammatory hyperpigmentation.

As used herein, "blotchiness" means a condition of the skin associated with redness or erythema.

As used herein, "age spots" means a condition of the skin associated with discrete pigmentation, e.g., small areas of darker pigmentation that may develop on the face as well as the hands.

As used herein, "cosmetic" refers to a beautifying substance or preparation which preserves, restores, bestows, simulates, or enhances the appearance of bodily beauty or appears to enhance the beauty or youthfulness, specifically as it relates to the appearance of tissue or skin.

As used herein, "cosmetically effective amount" means an amount of a physiologically active compound or composition sufficient for treating one or more signs of skin aging, but low enough to avoid serious side effects. The cosmetically effective amount of the compound or composition will vary with the particular condition being treated, the age and physical condition of the end user, the severity of the condition being treated/prevented, the duration of the treatment, the nature of other treatments, the specific compound or product/composition employed, the particular cosmetically-acceptable carrier utilized, and like factors.

It is believed that one skilled in the art can, based upon the description herein, utilize the present invention to its fullest extent. The following specific embodiments are to be construed as merely illustrative, and not limitative of the remainder of the disclosure in any way whatsoever.

Tropoelastin Promoter

"Tropoelastin promoter," as used herein, refers to a class of compounds that possess the biological activity of enhancing the production of tropoelastin. Tropoelastin promoters, according to the present invention, include all natural or synthetic compounds that are capable of enhancing the production of tropoelastin in the human body.

Suitable tropoelastin promoters may be determined, for example, using the "Tropoelastin Promoter Assay" as follows.

A cardiomyoblast cell line, H9c2, ($2 \times 10^4$ cells/well) is grown in a 48-well plate for 24 hours to reach 80-90% confluence. The next day, the cells are transiently transfected with the pGL2-Elastin2.2 luciferase reporter construct at a concentration of 0.45 μg total DNA in the ratio 6:1 pGL:pRL, using Lipofectamine 2000, following manufacturer's instructions (Invitrogen Corporation, Carlsbad, Calif.). A construct with the Renilla luciferase reporter gene (pRL-TK) is included as an internal control in all transfections. One day after transfection, the cells are treated with the indicated dose of the test sample for 24 hours before they are lysed for analysis. Luciferase assays are carried out using the Dual-Luciferase Reporter Assay System from Promega, following manufacturer's protocol. The ratio of firefly and renilla luciferase activities (RLU) is used to evaluate the Tropoelastin Promoter Activity of the test samples. Specifically, the ratio of firefly to renilla luciferase activities (RLU) for the sample is divided by the RLU measured for the vehicle control to arrive at Tropoelastin Promoter Activity for the test sample.

Preferably, the tropoelastin promoter has a Tropoelastin Promoter Activity of at least 1.2, preferably at least 1.25, more preferably at least 1.3, and most preferably at least 1.5; when tested in one or more concentrations in a range of 0.5 micrograms/milliliter to 2.5 milligrams per milliliter (on an actives basis), preferably when tested in a concentration in the range of 1.0 micrograms/milliliter to 2.5 milligrams per milliliter (on an actives basis).

Examples of suitable tropoelastin promoters include, but not limited to, blackberry extract, cotinus extract, a feverfew extract, and bimetal complexes having copper and/or zinc constituents. The bimetal complex having copper and/or zinc constituents may be, for example, copper-zinc citrate, copper-zinc oxalate, copper-zinc tartarate, copper-zinc malate, copper-zinc succinate, copper-zinc malonate, copper-zinc maleate, copper-zinc aspartate, copper-zinc glutamate, copper-zinc glutarate, copper-zinc fumarate, copper-zinc glucarate, copper-zinc polyacrylic acid, copper-zinc adipate, copper-zinc pimelate, copper-zinc suberate, copper-zinc azealate, copper-zinc sebacate, copper-zinc dodecanoate, or combinations thereof. In a preferred embodiment, the tropoelastin promoter is selected from blackberry extracts, cotinus extracts, feverfew extracts, and combinations thereof.

By "cotinus extract," it is meant an extract of the plant *Cotinus coggygria*, such as a water extract of *Cotinus coggygria*, 3% active, that is commercially available from Bilkokoop of Sofia, Bulgaria.

By "feverfew extract," it is meant an extract of the plant *Tanacetum parthenium*, such as may be prepared as set forth in published US Patent Application No. US2007/0196523. One particularly suitable feverfew extract is commercially available as about 20% active feverfew extract, from Integrated Botanical Technologies of Ossining, N.Y.

A particularly preferred tropoelastin promoter is a blackberry extract. By "blackberry extract," it is meant an extract of a plant of the genus *Rubus*, and preferably *Rubus fruticosus*. In one embodiment, the extract is isolated from the flowers of the plant. In a further embodiment, the extract is isolated from dried flowers of the plant. Such extracts may be isolated from one or more parts of the plant (e.g., the whole plant, flower, seed, root, rhizome, stem, fruit and/or leaf of the plant). In a preferred embodiment, the blackberry extract is a blackberry leaf extract.

The extraction process may include physically removing a piece of such plant, and, for example, grinding it. Suitable compounds may also be isolated from the plant by using extraction procedures well known in the art, e.g., the use of organic solvents such as lower $C_1$-$C_8$ alcohols, $C_1$-$C_8$ alkyl polyols, $C_1$-$C_8$ alkyl ketones, $C_1$-$C_8$ alkyl ethers, acetic acid $C_1$-$C_8$ alkyl esters, and chloroform, and/or inorganic solvents such as water, inorganic acids such as hydrochloric acid, and inorganic bases such as sodium hydroxide.

For example, a blackberry extract may be prepared by an extraction with water, alcohols such as ethanol, or combination thereof. It is preferred to use an extractant including both ethanol and water.

The blackberry plant parts are preferably dried prior to extraction. It is preferable to use only the leaves of the blackberry plant and not other plant parts such as the fruit (berries) of the blackberry, its branches, or roots.

In one embodiment, blackberry leaf extract is prepared as follows: a) an extractant containing an alcohol selected from the group consisting of methanol, ethanol, n-propanol, and isopropanol is added to blackberry leaves, and b) the blackberry leaves are contacted with the extractant for up to 72 hours.

The ratio of the mass of extractant to leaf solids is preferably established such that at least a 10-fold mass of extractant relative to the leaf solids but preferably no more than a 50-fold mass of extractant relative to the leaf solids is obtained, preferably a 10- to 20-fold mass. A 14- to 18-fold mass of extractant relative to the leaf solids is particularly preferable. Good results were achieved with a 16-fold mass of an ethanol-containing solvent (relative to the leaf solids).

The time for performing extraction step b) is at most 72 hours but can also be shorter. With particularly short extraction times only a very dilute extract is obtained in step b). It is therefore preferable to extract the blackberry leaves in step b) for at least 1 hour, in particular for at least 2 hours. The necessary extraction time is chosen on the basis of the quality of the blackberry leaves to be extracted, particularly their age, and of the other extraction conditions, particularly the extraction temperature. At elevated extraction temperatures, in particular at an extraction temperature in the range from 60 to 100° C., preferably in the range from 80 to 100° C., the extraction time is preferably 1 hour to 6 hours, particularly 2 hours to 4 hours.

In addition, it is particularly preferable to perform the extraction in step b) by refluxing the extractant, particularly at temperatures up to about 100° C., preferably in the range from 80 to 100° C. In this case the extraction time is preferably no more than 24 hours.

The extraction temperature is established on the basis of the extractant that is used. If an ethanol-containing solvent is used, a temperature in the range of 60° C. to 100° C., in particular in the range of 80° C. to 100° C., is preferred, particularly if a mixture of ethanol and water is used as the extractant as described below.

It is preferable if the extractant contains an alcohol, particularly ethanol, in an amount of at least 20 wt. % relative to the total weight of extractant. It is likewise preferable if the extractant contains water in an amount of at least 15 wt. % relative to the total weight of extractant. It is particularly preferable if the extractant simultaneously contains at least 20 wt. % of an alcohol (preferably ethanol) and at least 15 wt. % of water relative to the total weight of extractant.

Particularly preferred blackberry leaf extracts are obtained with an extractant consisting of ethanol and water in a weight ratio of 2:8 (2 parts by weight of ethanol mixed with 8 parts by weight of water) to 8:2, preferably in a weight ratio of 3:7 to 7:3, particularly preferably in a weight ratio of 3:7 to 1:1.

Detailed procedures for preparing a suitable blackberry leaf extract are disclosed in published US Patent Application No. 2008/0095719, which is herein incorporated in its entirety.

Accordingly, in one preferred embodiment, the blackberry extract is a blackberry leaf extract, i.e., the extract is produced from the leaves of the blackberry plant. In a particularly preferred embodiment, the blackberry extract is produced from the leaves of *Rubus fruticosus*. In a further particularly preferred embodiment, the blackberry extract is produced by extracting the leaves of *Rubus fruticosus* with a mixture of water and a lower alcohol such as ethanol.

One particularly suitable blackberry extract produced by extracting the leaves of *Rubus fruticosus* with a mixture of water and ethanol is the commercially available material "SymMatrix" from Symrise, Inc. of Teterboro, N.J., which is compounded to about 5 to 10% by weight in a maltodextrin matrix.

Compositions of the present invention may include a cosmetically effective amount of one or more tropoelastin promoters such as those described above. The compositions preferably include, on an active basis, from about 0.1% to about 10% by weight of tropoelastin promoters, more preferably from about 0.5% to about 5% by weight of tropoelastin promoters, and most preferably from about 0.5% to about 2% by weight of tropoelastin promoters.

Tropoelastin Crosslinker

Compositions of the present invention include one or more tropoelastin cross-linkers. By "tropoelastin crosslinker," it is meant a class of compounds that possess the biological activity of enhancing the enzymatically-based cross-linking of elastin precursors such as tropelastin, fibrilin and the like to one another or onto other elastin precursors or onto existing elastic fibers.

In one embodiment, the tropoelastin crosslinker is suitable to promote the activity of an isoform of lysyl oxidase (such as LOXL, lysyl-oxidase like isoform) as described in published patent application, GB2402676 of Colectica, which is incorporated herein by reference in its entirety.

Particularly suitable examples of tropoelastin cross-linkers include natural or synthetic compounds, such as, but not limited to, dill extract, currant extract, cardamom extract, black radish extract, box holly extract, Asafoetida extracts (e.g., gum), ethyl hexenoate, methyl butyrate, and ethyl decadienoate. One particularly suitable tropoelastin cross-linker is dill extract.

In a preferred embodiment, compositions of the present invention include a cosmetically effective amount of a dill extract. By "dill extract," it is meant an extract of a plant of the genus *Peucedanum*, and preferably *Peucedanum graveolens*. The extract may be one of the whole plant, flower, seed, root, rhizome, stem, fruit and/or leaf of the plant, such as may be prepared by grinding or chemical extraction. In a preferred embodiment, the dill extract is an extract of the fruit of dill, preferably of *Peucedanum graveolens*.

Such compounds may also be isolated from the plant by using extraction procedures well known in the art, e.g., the use of organic solvents such as lower $C_1$-$C_8$ alcohols, $C_1$-$C_8$ alkyl polyols, $C_1$-$C_8$ alkyl ketones, $C_1$-$C_8$ alkyl ethers, acetic acid $C_1$-$C_8$ alkyl esters, and chloroform, and/or inorganic solvents such as water, inorganic acids such as hydrochloric acid, and inorganic bases such as sodium hydroxide.

One particularly suitable dill extract is a "dill fruit," 5%-10% in water, commercially available from BASF of Parsippany, N.J., as "Lys'lastin."

In one embodiment, the composition preferably includes, on an active basis, from about 0.1% to about 10% by weight of tropoelastin crosslinker, more preferably from about 0.5% to about 5% by weight of tropoelastin crosslinker, and most preferably from about 0.5% to about 2% by weight of tropoelastin crosslinker.

According to the invention, surprising and synergistic effects in treating one or more signs of skin aging are achieved using the composition of the invention. In particular, topical application of the composition of the invention improves the properties of skin, such as decreasing lines and wrinkles, increasing elasticity, and reducing uneven skin tone, blotchiness or age spots.

It should be noted that the tropoelastin promoter and tropoelastin cross-linker may be two or more separate compounds. Alternatively, they may be a single compound having both tropoelastin promoting activity and tropoelastin cross-linking activity.

Cosmetically Acceptable Carriers

One or more cosmetically acceptable carriers may also be present in the cosmetic compositions of this invention.

As used herein, "cosmetically acceptable" means suitable for use in contact with (human) tissues (e.g., the skin) without undue toxicity, incompatibility, instability, irritation, allergic response, and the like, commensurate with a reasonable benefit/risk ratio.

Suitable carriers of this invention include, but are not limited to, water, ethanol, isopropanol, 1,2-propanediol, glycerin, benzyl alcohol, dimethylisosorbide, triacetin, glycol ethers, propylene glycol and polyethylene glycol (PEG). Particularly preferred solvents include PEG having an average molecular weight between about 200 and about 400, castor oil, triacetin, dimethylisosorbide, ethanol, and water, and combinations thereof. The cosmetically acceptable carrier constitutes from about 50% to about 99.99%, by weight, of the composition, more preferably from about 80% to about 95%, by weight, of the composition. In a particularly preferred embodiment, the composition includes at least about 25% by weight water, more preferably at least about 50% by weight water.

Various compounds may be added to the formulation to alter osmolarity and/or pH to acceptable levels. These include, but are not limited to, mannitol, sucrose, calcium chloride, sodium chloride, sodium phosphate monobasic, sodium phosphate dibasic, sodium hydroxide, and hydrochloric acid.

The compositions may be made into a wide variety of cosmetic articles that include but are not limited to lotions, creams, gels, sticks, sprays, ointments, cleansing liquid washes and solid bars, shampoos and hair conditioners, pastes, foams, powders, mousses, shaving creams, wipes, strips, patches, electrically-powered patches, wound dressing and adhesive bandages, hydrogels, film-forming products, facial and skin masks, make-up such as foundations, eye liners, and eye shadows, and the like.

These product types may contain several types of cosmetically acceptable carriers including, but not limited to solutions, suspensions, emulsions such as microemulsions and nanoemulsions, gels, solids and liposomes. Other carriers can be formulated by those of ordinary skill in the art. In order to facilitate the formulation of a suitable vehicle, one may include any of various functional ingredients in the composition. For example, one may include any of a number of emollients, humectants, pH adjusters, sequesterants, emulsifiers, wetting agents, thickeners, polymers, preservatives, colorants, fragrances, and other ingredients commonly used in personal care and cosmetic products. The pH chosen is not critical, but may be in a range, for example that is from about 4 to about 8, such as from about 5 to about 7.

Additional Cosmetically Active Agents

In one embodiment, the compositions according to this invention may further contain one or more additional cosmetically active agent(s) as well as the above-mentioned components. What is meant by a "cosmetically active agent" is a compound, which may be a synthetic compound or a compound extracted, isolated, purified or concentrated from a natural source, or a natural extract containing a mixture of compounds, that has a cosmetic or therapeutic effect on the tissue, including, but not limited to: anti-microbial agents such as anti-yeast, anti-fungal, and anti-bacterial agents, anti-inflammatory agents, anti-aging agents, anti-parasite agents, antioxidants, keratolytic agents, nutrients, vitamins, minerals, energy enhancers, and the like.

Examples of vitamins that may be constituents of the compositions of this invention include, but are not limited to, vitamin A, vitamin Bs such as vitamin B3, vitamin B5, vitamin B7 and vitamin B12, vitamin C, vitamin K, vitamin E such as alpha, gamma or delta-tocopherol, and their derivatives (such as salts and esters) and mixtures thereof.

Examples of antioxidants which may be utilized in the compositions and methods of this invention include, but are not limited to, water-soluble antioxidants such as sulfhydryl compounds and their derivatives (e.g., sodium metabisulfite and N-acetyl-cysteine), lipoic acid and dihydrolipoic acid, resveratrol, lactoferrin, and ascorbic acid and ascorbic acid derivatives (e.g., ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), different types of tocopherols (e.g., alpha-, gamma-, and delta-tocopherols and their esters such as acetate) and their mixtures, tocotrienols, and ubiquinone. Natural extracts containing antioxidants suitable for use in the compositions of this invention include, but are not limited to, extracts containing flavinoid, isoflavinoid, and their derivatives such as genistein and diadzein (e.g., such as soy and clover extracts, extracts containing resveratrol and the like.

Other Materials

Various other materials may also be present in the compositions useful in the subject invention. These include proteins and polypeptides, preservatives and an alkaline agent. Examples of such agents are disclosed in the 2008 International Cosmetic Ingredient Dictionary and Handbook, 12th Edition published by the Personal Care Products Council).

The present invention is further defined in the following Examples. It should be understood that these Examples, while indicating preferred embodiments of the invention, are given by way of illustration only.

EXAMPLES

Example I

Tropoelastin Promotion Assay

Various samples were prepared using the following extracts: *Continus coggygria* (from Bilkokoop of Sofia, Bulgaria), *Tanacetum parthenium* (20% active, parthenolide-free feverfew extract from Integrated Botanical Technologies of Ossining, N.Y.), *Rubus fruticosus* (10% active, SymMatrix, from Symrise), and *Peucedanum graveolens* (10% active, Lys'lastin, from BASF). The extracts were diluted in cell culture media (DMEM Media of Invitrogen, San Diego Calif.) to the concentration of "active" extract as indicated in Table 1 below. Blackberry extract was pre-diluted in sufficient ethanol in order to prepare a homogeneous mixture prior to dilution with cell culture media. The concentration of ethanol in the samples was about 1%.

Each sample was subjected to the Tropoelastin Promoter Assay. The results are shown in Table 1.

TABLE 1

| Extract | Concentration (on active basis) | Increase in Tropoelastin Promoter Activity |
| --- | --- | --- |
| *Continus coggygria* | 15 ug/ml | 1.57 ± 0.24 * |
| *Tanacetum parthenium* | 20 ug/ml | 1.54 ± .011 * |
| *Tanacetum parthenium* | 5 ug/ml | 1.27 ± .024 |
| *Rubus fruticosus* | 5 ug/ml | 1.73 ± .026 * |
| *Rubus fruticosus* | 0.5 ug/ml | 1.33 ± .019 |
| *Peucedanum graveolens* | 2.5 mg/ml | 0.95 ± 0.11 |
| Vehicle Control (Ethanol) | 0.01% | 1.0 ± 0.10 |

* = P < 0.05 using a Student's t-Test

The blackberry extract provided the greatest tropoelastin promotion, followed by significant tropoelastin promotion for the feverfew extract and the cotinus extract. In contrast, the dill extract, even at a high concentration, provided no tropoelastin promotion.

Example II

Preparation of Compositions

The following compositions according to the invention, Compositions 1 and 2, were prepared using the ingredients shown in Table 2 and Table 3, respectively.

TABLE 2

Composition 1

| INCI Name | Trade Name | Percentage |
| --- | --- | --- |
| WATER | PURIFIED WATER | 68.95 |
| Ultrez 10 | Carbomer | 0.60 |
| Disodium EDTA | VERSENE NA | 0.20 |
| Steareth-2 | Brij 72 | 0.75 |
| Steareth-21 | Brij 721 | 1.50 |
| C12-15 Alkyl Benzoate | Finsolv TN | 2.00 |
| Dow Corning Q7-9120 Silicone Fluide (20 cst) | Dimethicone | 5.00 |
| Phenonip XB | Phenonip XB | 1.00 |
| *Peucedanum graveolens* (10% active) | Lys'Lastine | 10.00 |
| Maltodextrin, *Rubus Fruticosus* (Blackberry) Leaf Extract (10% active) | SymMatrix | 10.00 |

VERSENE is available from Dow Chemical of Midland, Michigan.
ULTREZ/CARBOMER is available from Lubrizol Corporation of Wickliffe, Ohio
BRIJ is available from ICI-Uniquema-AkzoNobel of Amsterdam, Netherlands
FINSOLV is available from Finetex Corporation of Elmwood, Park, NJ
MIRASIL is available from Rhodia Group of Cranbury, NJ
PHENONIP is available from Clariant Functional Chemicals of Woodlands, Texas
LYS'LASTINE is available from BASF of Parsippany, New Jersey
SymMatrix is available from Symrise Inc. of Teterboro, NJ Composition 1 was prepared as follows. An oil phase was prepared by adding C 12-15 alkyl benzoate to a clean glass beaker. Agitation was begun and the vessel was heated to 55-60° C. When the oil phase reached 55 C or higher, Brij 72 and Brij 721 were added. When the oil phase reached 55-60° C., it was held at that temperature and mixed for 15 min (or until uniform). The temperature was then held at 55-60° C. with mixing until addition to water phase.

A water phase was prepared by adding water to a clean glass beaker. Agitation was begun and the vessel was heated to 55-60° C. Disodium EDTA and Ultrez 10 were added. At 55-60° C., the ingredients were mixed for 15 min or until homogeneous. The temperature was then held at 55-60° C. with mixing for phasing.

The oil phase was added to the water phase with increased agitation and then mixed at high speed for 10-20 min. At 50° C. or lower, dimethicone was added. At 40° C. or lower, Phenonip XB was added. The phases were then mixed for 10 min or until uniform. Sodium hydroxide was added (target pH was 5.4). The composition was then mixed for 10 min or until uniform. Lys'Lastine and SymMatrix were then added. This was mixed until uniform. Water was then added to QS and the composition was then mixed for 10 minutes. The concentration of blackberry extract and dill extract, on an actives basis, in the final composition were each 1%.

TABLE 3

Composition 2

| INCI Name | Trade Name | Percentage |
| --- | --- | --- |
| Water | Water, demineralized | 41.47312 |
| Water, Hydroxyethyl Urea, ammonium lactate | Hydrovance | 2.00000 |
| Glycerin | Glycerin 99.5% | 4.00000 |
| Disodium EDTA | Disodium EDTA | 0.10000 |
| Scleroticum Gum | Amigel | 0.50000 |
| Caffeine | Caffeine | 2.00000 |
| Water, Hydroxypropyl, Starch Phosphate | Structure XL | 3.70000 |
| Sodium Hydroxide | Sodium Hydroxide 100% | 0.00650 |
| Methylparaben | Methylparaben | 0.20000 |
| Isodecyl Neopentanoate | DUB VCI 10 | 2.00000 |
| Isononyl Isononanoate | Isononyl Isononanoate | 4.00000 |
| Dimethicone | Mirasil DM 100 | 1.00000 |
| Cetyl Alcohol. Glyceral Stearate. Steareth-20. Ceteth-20. PEG-75 Stearate | Emulium Delta | 3.00000 |
| BHT | BHT | 0.07000 |
| Propylparaben | Propylparaben | 0.20000 |
| Ethylparaben | Ethylparaben | 0.15000 |
| Tocopheryl Acetate | Tocopheryl Acetate | 0.10000 |
| Dimethicone | DC 1413 | 2.00000 |
| Cyclopentasiloxane | Cyclopentasiloxane | 3.00000 |
| Aqua• methyl methacrylate crosspolymer | Micropearl M305 | 1.00000 |
| Phenoxyethanol | Phenoxyethanol | 0.50000 |
| PEG-8 | PEG-8 | 5.00000 |
| Maltodextrin, *Rubus Fruticosus* (Blackberry) Leaf Extract (10% active) | Symmatrix | 10.0000 |
| *Peucedanum graveolens* (10% active) | LysLastine | 10.00000 |
| CI 14700 | FD&C Red No. 4 | 0.00038 |
| Alcohol. Aqua | Alcool ethylique surfin 96 | 5.00000 |

HYDROVANCE and STRUCTURE XL are available from AkzoNobel.
AMIGEL is available from Alban Muller International of Miami, Florida.
Methyl paraben is available from Alfa Aesar of Ward Hill, Massachusetts
DUB VCI is available from Stearinerie Dubois of Aylesbury, UK
EMULIUM is available from Gattefosse of St-Priest, France
DC1413 is available from Dow Corning of Midland, Michigan
MICROPEARL is available from Seppic of Fairfield, New Jersey Composition 2 was prepared as follows. An oil phase was prepared by adding to a vessel DUB VCI, isononyl isonanoate, MIRASIL, EMULIUM, BHT, propylparaben, ethylpataben, and tocopherol acetate while mixing and heating to 80° C.

A water phase was prepared by adding water to a vessel and adding STRUCURE XL and EDTA. Heat was applied and HYDROVANCE and glycerin were added. When the water phase reached 40° C., AMIGEL was added. When the water phase reached 75° C., caffeine and methylparaben were added.

The water phase and oil phase were combined at 80° C. and allowed to cool. At 35° C. MICROPEARL, phenoxyethanol, fragrance, PEG-8, retinol, and CL 14700 were added. When the mixture cooled to 20° C. alcohol was added. The concentration of blackberry extract and dill extract, on an actives basis, in the final composition were each 1%.

A Comparative Composition A (placebo) was prepared using ingredients shown in shown in Table 4.

TABLE 4

Comparative Composition A

| CTFA Name | Trade Material | Percentage |
|---|---|---|
| Propylene Glycol | Propylene Glycol | 25.00 |
| Water | Purified water | 61.45 |
| Disodium EDTA | VERSENE NA | 1.00 |
| Glycerin 917 | Glycerine | 3.00 |
| Dimethicone | DC 200 Fluid 100 cst | 2.00 |
| BHT | BHT | 0.05 |
| Polyacrylamide & Laureth 7 & C13-14 Isoparrafin | Sepigel 305 | 6.50 |
| Phenonip XB | Phenonip XB | 1.00 |

DC 200 Fluid 100 cst is available from Dow Corning of Midland, Michigan
SEPIGEL 305 is available from Seppic of Fairfield, New Jersey Comparative Composition A was made as follows. Water and propylene glycol were added to a clean glass beaker and agitation was begun. The vessel was heated to 40-45° C. This water phase was mixed for 15 minutes or until homogeneous. BHT, Glycerin, and DC 200 Fluid were then added and mixed at high speed for 10-20 min. This was allowed to cool. At 40° C. or lower, Phenonip XB was added. This was mixed for 10 min or until uniform. Sepigel 305 was then added and the ingredients were mixed for 10 min or until uniform and then allowed to cool to room temperature. This sample served as a placebo (no active).

A Comparative Composition B was prepared using ingredients shown in shown in Table 5.

TABLE 5

Comparative Composition B

| CTFA Name | Trade Material | Percentage |
|---|---|---|
| Cotinus(10% symrise extract) | Cotinus(10% symrise extract) | 20.00 |
| Water | Purified water | 66.45 |
| Disodium EDTA | VERSENE NA | 1.00 |
| Glycerin 917 | Glycerine | 3.00 |
| Dimethicone | DC 200 Fluid 100 cst | 2.00 |
| BHT | BHT | 0.05 |
| Polyacrylamide & Laureth 7 & C13-1 | Sepigel 305 | 6.50 |
| Phenonip XB | Phenonip XB | 1.00 |

Cotinus (10% extact in water) is available from Symrise Inc. of Teterboro, NJ

Comparative Composition B was prepared in a manner similar to Comparative Composition A, except that Cotinus extract was added to the vessel after it had cooled to room temperature and the mixture was mixed for another 10 minutes. The final composition had a concentration of Cotinus extract of 2%, on an actives basis.

A Comparative Composition C was prepared using ingredients identical to those shown for Comparative Composition A, except that 20% of *Rubus fructicosis* extract was included and a corresponding amount of water was excluded. *Rubus fructicosis* extract was premixed into a slurry with the propylene glycol and this premix was added to the vessel after the batch had cooled to room temperature, following which the mixture was mixed for another 10 minutes. The final composition had a concentration of *Rubus fructicosis* extract that was 2%, on an actives basis.

A Comparative Composition D was prepared using ingredients identical to those shown for Comparative Composition A, except that 10% of Lys'Lastine (dill extract) was included and a corresponding amount of water was excluded. The Lys'Lastine was premixed into a slurry with the propylene glycol and this premix was added to the vessel after the batch had cooled to room temperature, following which the mixture was mixed for another 10 minutes. The final composition had a concentration of Lys'Lastine that was 1%, on an actives basis.

Cutometer Test

Compositions 1 and 2, and Comparative Compositions A-D were used in a clinical study conducted with 50 human subjects (female, between the ages of 35 and 50). Each subject was randomly assigned two different compositions to use over the course of the study. Following treatment with the compositions, the subjects were subjected to a cutometer test as described below. The cutometer test provides an in-vivo, quantitative measurement of properties associated with skin elasticity.

On each of the subjects, a pea-size amount of a first composition was applied on the upper-inner arm twice daily for 12 weeks. A second composition was applied on the subject's other arm in the same manner. Cutometer SEM 580 (available from Courage & Khazaka of Koln, Germany) measurements were taken on the center of each upper-inner arm to assess the visco-elastic properties of the skin at the site of application. The instrument applied a 400 mbar vacuum through a 2-millimeter probe to a small area of skin for two seconds. The elastic response of the skin was then measured by an optical technique. This method provides the following deformation parameters relating to skin elasticity: "Gross Elasticity" and "Elastic Recovery Rate."

The results of are shown in Table 6.

TABLE 6

CUTOMETER TEST RESULTS

| Test Material | Concentration (actives basis, %) | Gross Elasticity ($\times 10^{-3}$) | Net Increase in Elastic Recovery Rate ($\times 10^{-3}$) |
|---|---|---|---|
| Comp. A (Placebo) | — | 5 | 0 |
| Comp. B (*Continus coggygria*) | 2% | 9 | 2 |
| Comp. D (*Peucedanum graveolens*) | 1% | 1 | −14 |
| Comp. C (*Rubus fruticosus*) | 2% | 9 | 8 |
| Comp. 1 (*Peucedanum graveolens* and *Rubus fruticosus*) | 1% of each extract | 33* | 21** |

*= $P < 0.05$ significance versus placebo using a Student's t-Test
**= $P < 0.1$ significance versus placebo using a Student's t-Test Quite surprisingly, Composition 1 containing both 1% *Rubus fruticosus* and 1% *Peucedanum graveolens* demonstrated a synergistic improvement in skin elasticity. The combined effect was greater than the sum of the separate effects of even 2% *Rubus fruticosus* and 1% *Peucedanum graveolens* alone. In fact, the improvement in elasticity for Composition 1 containing both 1% *Rubus fruticosus* and 1% *Peucedanum graveolens* was more than triple that of the sum of the separate effects of 2% *Rubus fruticosus* (Composition C) and 1% *Peucedanum graveolens* (Composition D). Furthermore, this surprising synergy held for both gross elasticity and net increase in elastic recovery.

What is claimed is:

1. A cosmetic composition comprising: (a) a blackberry leaf extract, (b) a dill extract, and (c) a cosmetically acceptable carrier; wherein said blackberry leaf extract and dill extract are each present in an amount comprising from about 0.1% to about 10% by weight of the composition.

2. The cosmetic composition according to claim 1, wherein said blackberry leaf extract has a tropoelastin promoter activity of at least about 1.2.

3. A method of treating a sign of skin aging comprising topically applying to the skin of a subject in need thereof a cosmetically effective amount of the composition according to claim 1.

4. The method of claim 3, wherein said blackberry leaf extract has a tropoelastin promoter activity of at least about 1.2.

* * * * *